(12) United States Patent
Friedman et al.

(10) Patent No.: US 8,014,571 B2
(45) Date of Patent: Sep. 6, 2011

(54) MULTIMODAL OCULAR BIOMETRIC SYSTEM

(75) Inventors: Marc D. Friedman, Needham, MA (US); Pablo Casaverde, Bedford, NH (US); Don Yansen, Lexington, MA (US); Tim McNerney, Newton, MA (US); Yasunari Tosa, Arlington, MA (US); David Usher, Waltham, MA (US); Nicholas A. Accomando, Hingham, MA (US); David Muller, Boston, MA (US); Greg Heacock, Auburn, WA (US); John Marshall, Farnborough (GB)

(73) Assignee: Identix Incorporated, Bloomington, MN (US)

( * ) Notice: Subject to any disclaimer, the term of this patent is extended or adjusted under 35 U.S.C. 154(b) by 1149 days.

(21) Appl. No.: 11/798,500

(22) Filed: May 14, 2007

(65) Prior Publication Data

US 2008/0044063 A1    Feb. 21, 2008

Related U.S. Application Data

(60) Provisional application No. 60/800,023, filed on May 15, 2006, provisional application No. 60/812,949, filed on Jun. 13, 2006, provisional application No. 60/819,630, filed on Jul. 11, 2006.

(51) Int. Cl.
  *G06K 9/00* (2006.01)
  *A61B 3/14* (2006.01)
  *A61B 3/10* (2006.01)

(52) U.S. Cl. ......... 382/117; 382/115; 351/206; 351/221

(58) Field of Classification Search .................. 382/117, 382/115, 118, 116, 124; 713/186, 182, 185, 713/150, 168, 176; 351/200, 205, 221, 206, 351/209; 340/5.1, 5.2, 5.52, 5.8, 5.81, 5.82, 340/5.83, 5.53; 356/71, 479; 600/506, 300, 481, 504; 707/999.006, 999.003; 726/26; 348/78; 902/3

See application file for complete search history.

(56) References Cited

U.S. PATENT DOCUMENTS

| | | | |
|---|---|---|---|
| 3,069,654 A | | 12/1962 | Hough |
| 4,641,349 A | | 2/1987 | Flom et al. |
| 5,291,560 A | | 3/1994 | Daugman |
| 5,359,669 A | * | 10/1994 | Shanley et al. ............... 382/117 |
| 5,572,596 A | | 11/1996 | Wildes et al. |
| 5,751,836 A | | 5/1998 | Wildes et al. |

(Continued)

OTHER PUBLICATIONS

Y. Park, et al.; "A Fast Circular Edge Detector for the Iris Region Segmentation"; S.-W. Lee, H.H. Buelthoff, T. Poggio (Eds.) BMCV 2000, LNCS 1811, pp. 417-423, May 2000.

(Continued)

*Primary Examiner* — Sheela C Chawan
(74) *Attorney, Agent, or Firm* — Nixon Peabody LLP

(57) ABSTRACT

A multimodal biometric identification system captures and processes images of both the iris and the retina for biometric identification. Another multimodal ocular system captures and processes images of the iris and/or the from both eyes of a subject. Biometrics based on data provided by these systems are more accurate and robust than using biometrics that include data from only the iris or only the retina from a single eye. An exemplary embodiment emits photons to the iris and the retina of both eyes, an iris image sensor that captures an image of the iris when the iris reflects the emitted light, a retina image sensor that captures an image of the retina when the retina reflects the emitted light, and a controller that controls the iris and the retina illumination sources, where the captured image of the iris and the captured image of the retina contain biometric data.

47 Claims, 11 Drawing Sheets

U.S. PATENT DOCUMENTS

| | | | |
|---|---|---|---|
| 5,859,686 | A | 1/1999 | Aboutalib et al. |
| 5,953,440 | A | 9/1999 | Zhang et al. |
| 6,122,394 | A * | 9/2000 | Neukermans et al. ........ 382/124 |
| 6,144,754 | A | 11/2000 | Okano et al. |
| 6,152,563 | A | 11/2000 | Hutchinson et al. |
| 6,215,891 | B1 | 4/2001 | Suzaki et al. |
| 6,229,907 | B1 | 5/2001 | Okano et al. |
| 6,247,813 | B1 | 6/2001 | Kim et al. |
| 6,285,780 | B1 | 9/2001 | Yamakita et al. |
| 6,289,113 | B1 * | 9/2001 | McHugh et al. ............. 382/117 |
| 6,373,968 | B2 | 4/2002 | Okano et al. |
| 6,526,160 | B1 | 2/2003 | Ito |
| 6,532,298 | B1 | 3/2003 | Cambier et al. |
| 6,542,624 | B1 | 4/2003 | Oda |
| 6,546,121 | B1 | 4/2003 | Oda |
| 6,571,002 | B1 | 5/2003 | Ogawa |
| 6,591,064 | B2 | 7/2003 | Higashiyama et al. |
| 6,597,377 | B1 | 7/2003 | MacPhail |
| 6,614,919 | B1 | 9/2003 | Suzaki et al. |
| 6,700,998 | B1 | 3/2004 | Murata |
| 6,714,665 | B1 | 3/2004 | Hanna et al. |
| 6,753,919 | B1 | 6/2004 | Daugman |
| 6,760,467 | B1 | 7/2004 | Min et al. |
| 6,785,406 | B1 | 8/2004 | Kamada |
| 6,850,631 | B1 | 2/2005 | Oda et al. |
| 6,944,318 | B1 | 9/2005 | Takata et al. |
| 6,992,717 | B2 | 1/2006 | Hatano |
| 7,099,495 | B2 | 8/2006 | Kodno et al. |
| 7,155,035 | B2 | 12/2006 | Kondo et al. |
| 7,197,166 | B2 | 3/2007 | Jeng |
| 7,277,561 | B2 | 10/2007 | Shin |
| 7,280,678 | B2 * | 10/2007 | Haven et al. .................. 382/117 |
| 7,404,640 | B2 * | 7/2008 | Ferguson et al. ............. 351/221 |
| 7,428,320 | B2 * | 9/2008 | Northcott et al. ............. 382/117 |
| 2002/0126881 | A1 | 9/2002 | Langley |
| 2003/0012413 | A1 | 1/2003 | Kusakari et al. |
| 2003/0117396 | A1 | 6/2003 | Yoon |
| 2004/0197011 | A1 | 10/2004 | Camus et al. |
| 2006/0008124 | A1 | 1/2006 | Ewe et al. |
| 2006/0147094 | A1 | 7/2006 | Yoo |
| 2006/0165266 | A1 | 7/2006 | Hamza |
| 2007/0036397 | A1 | 2/2007 | Hamza |
| 2007/0047772 | A1 | 3/2007 | Matey et al. |
| 2007/0047773 | A1 | 3/2007 | Martin et al. |
| 2007/0110284 | A1 | 5/2007 | Rieul et al. |
| 2007/0160266 | A1 | 7/2007 | Jones et al. |
| 2007/0160267 | A1 | 7/2007 | Jones et al. |

OTHER PUBLICATIONS

Christel-Loic Tisse, et al.; "Person identification technique using human iris recognition"; Advanced System Technology; Universite de Montpellier, May 2002.

Libor Masek; "Recognition of Human Iris Patterns for Biometric Identification"; School of Computer Science and Software Engineering, The University of Western Australia, 2003, pp. 1-56, May 12, 2006.

Xiaomei Liu, et al.; "Experiments with an Improved Iris Segmentation Algorithm"; Department of Computer Science and Engineering University of Notre Dame; Fourth IEEE Workshop on Automatic Identification Advanced Technologies (AutoID), Oct. 2005, New York, 6 pages.

Ping-Sung Liao, et al.; "A Fast Algorithm for Multilevel Thresholding"; Journal of Information Science and Engineering 17, pp. 713-727, Sep. 2001.

Nobuyuki Otsu; "A Threshold Selection Method from Gray-Level Histograms"; IEEE Transactions on Systems Man and Cybernetics, vol. SMC-9, No. I, Jan. 1979.

Int'l Search Report for PCT/US07/11507 which claims priority to U.S. Appl. No. 60/800,823; U.S. Appl. No. 60/812,949; and U.S. Appl. No. 60/819,630 (Jul. 11, 2008).

Written Opinion for PCT/US07/11507 which claims priority to U.S. Appl. No. 60/800,823; U.S. Appl. No. 60/812,949; and U.S. Appl. No. 60/819,630 (Jul. 11, 2008).

* cited by examiner

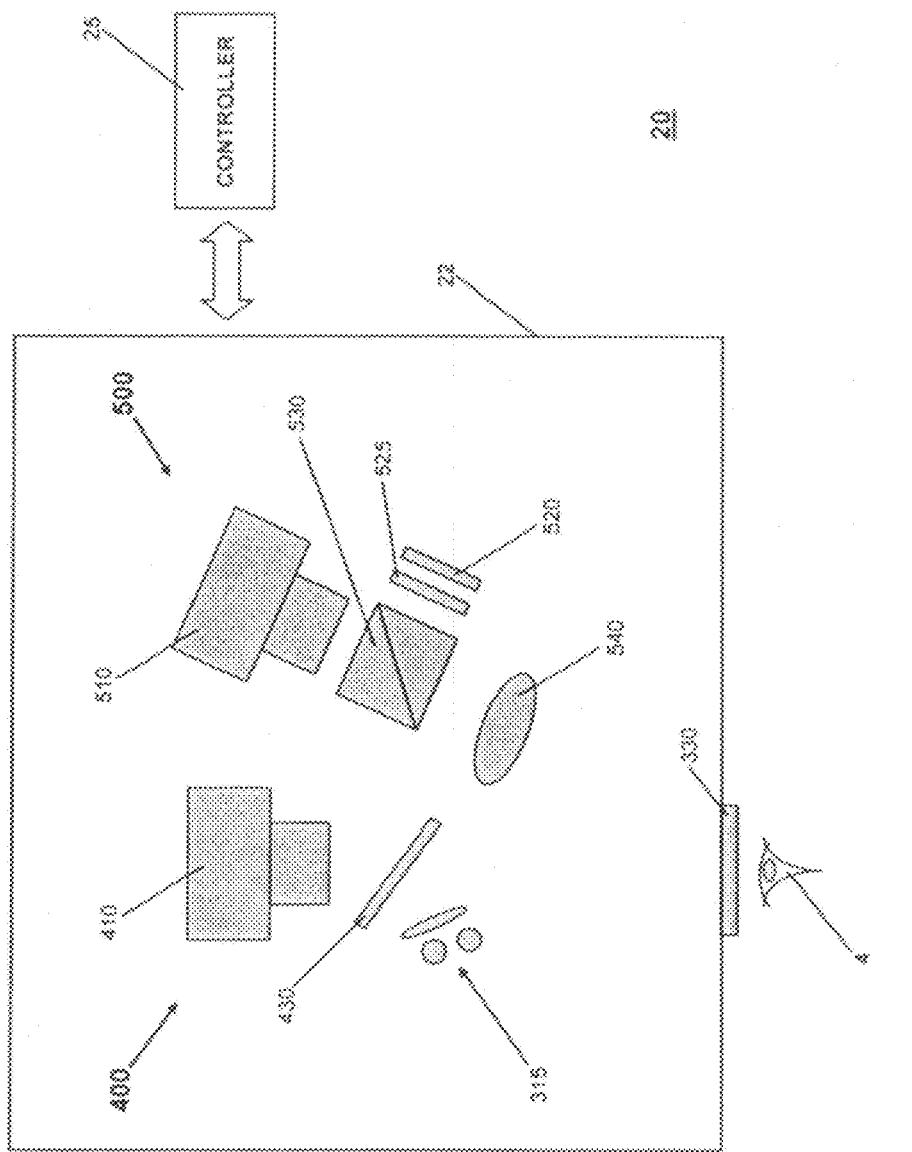

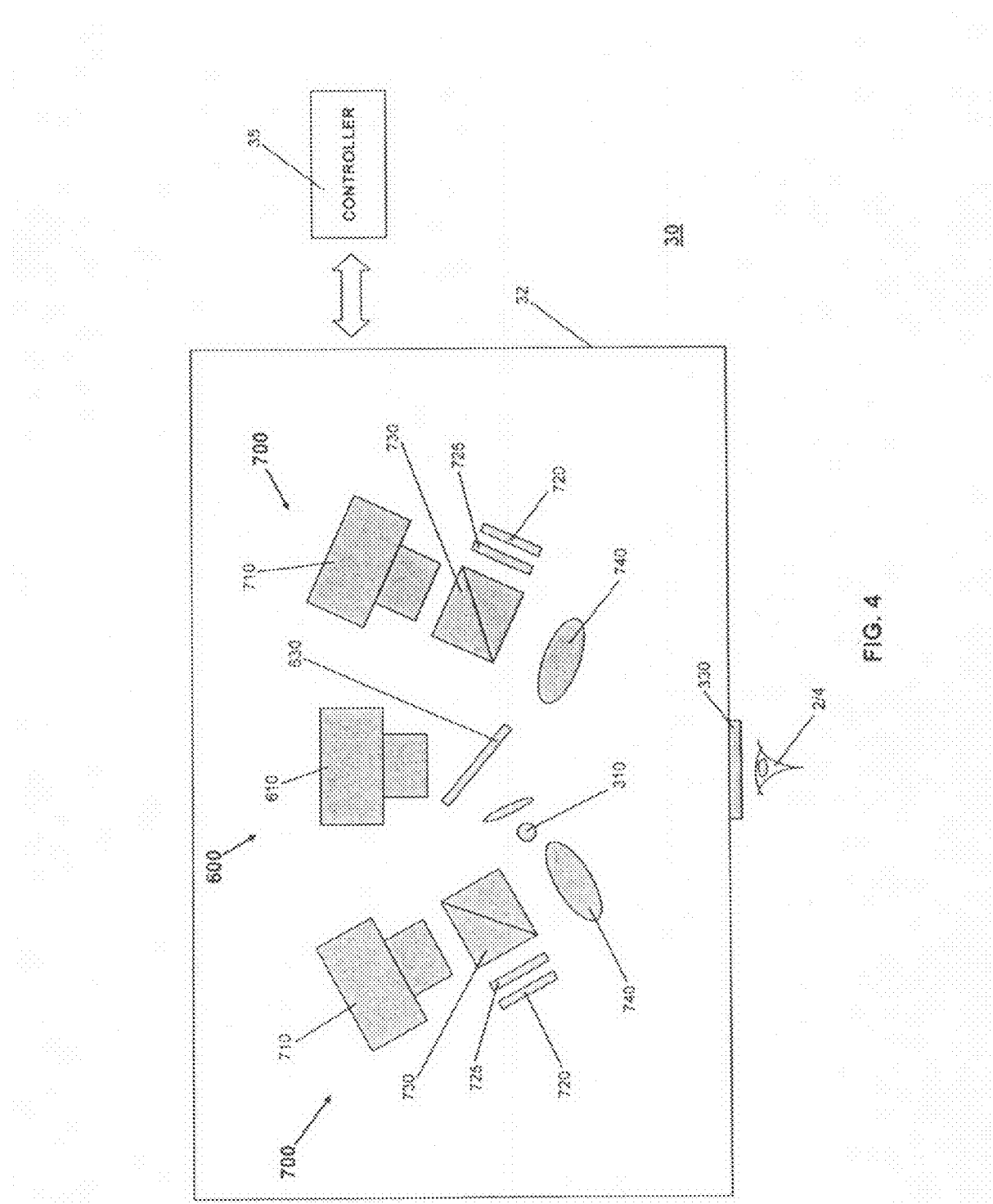

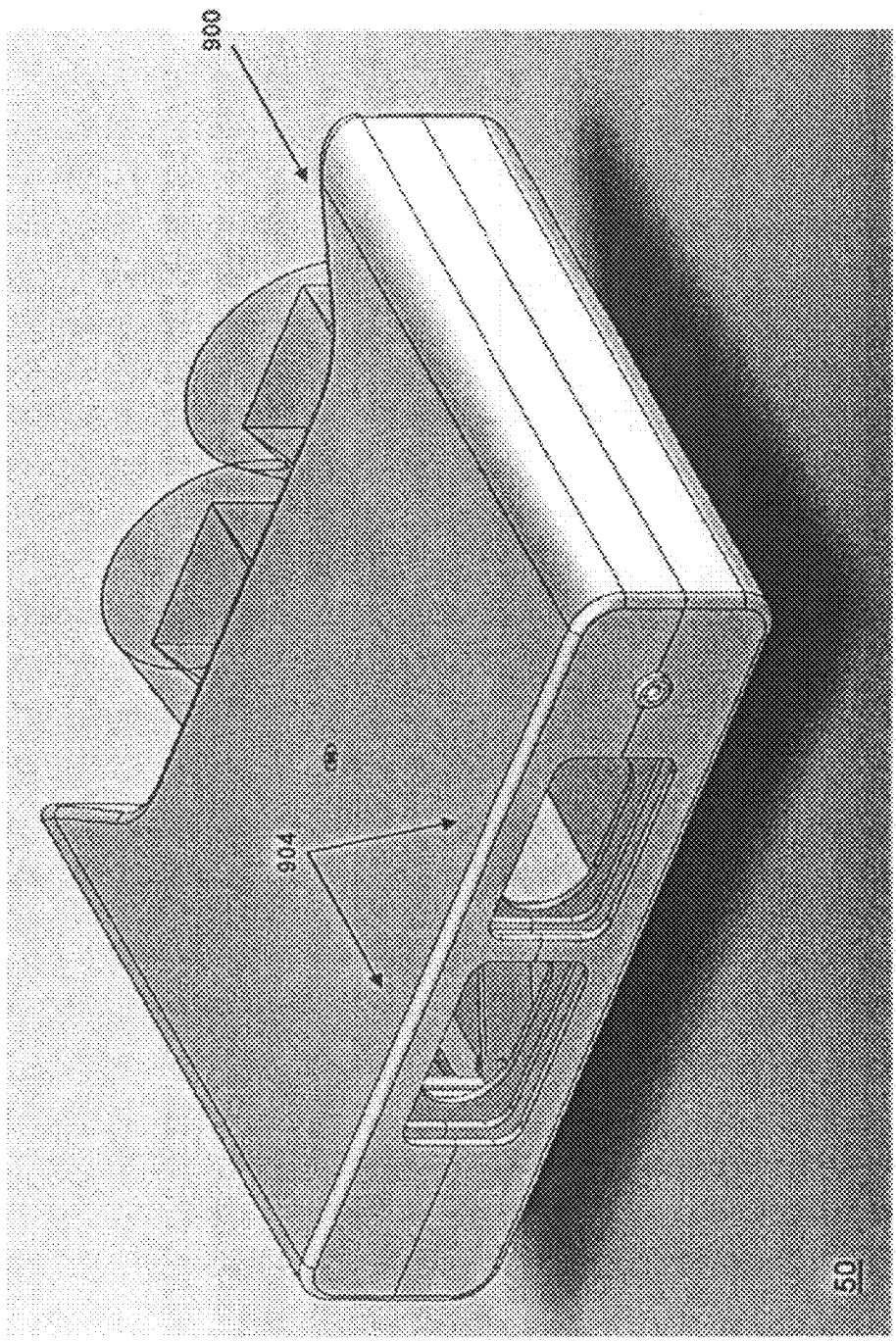

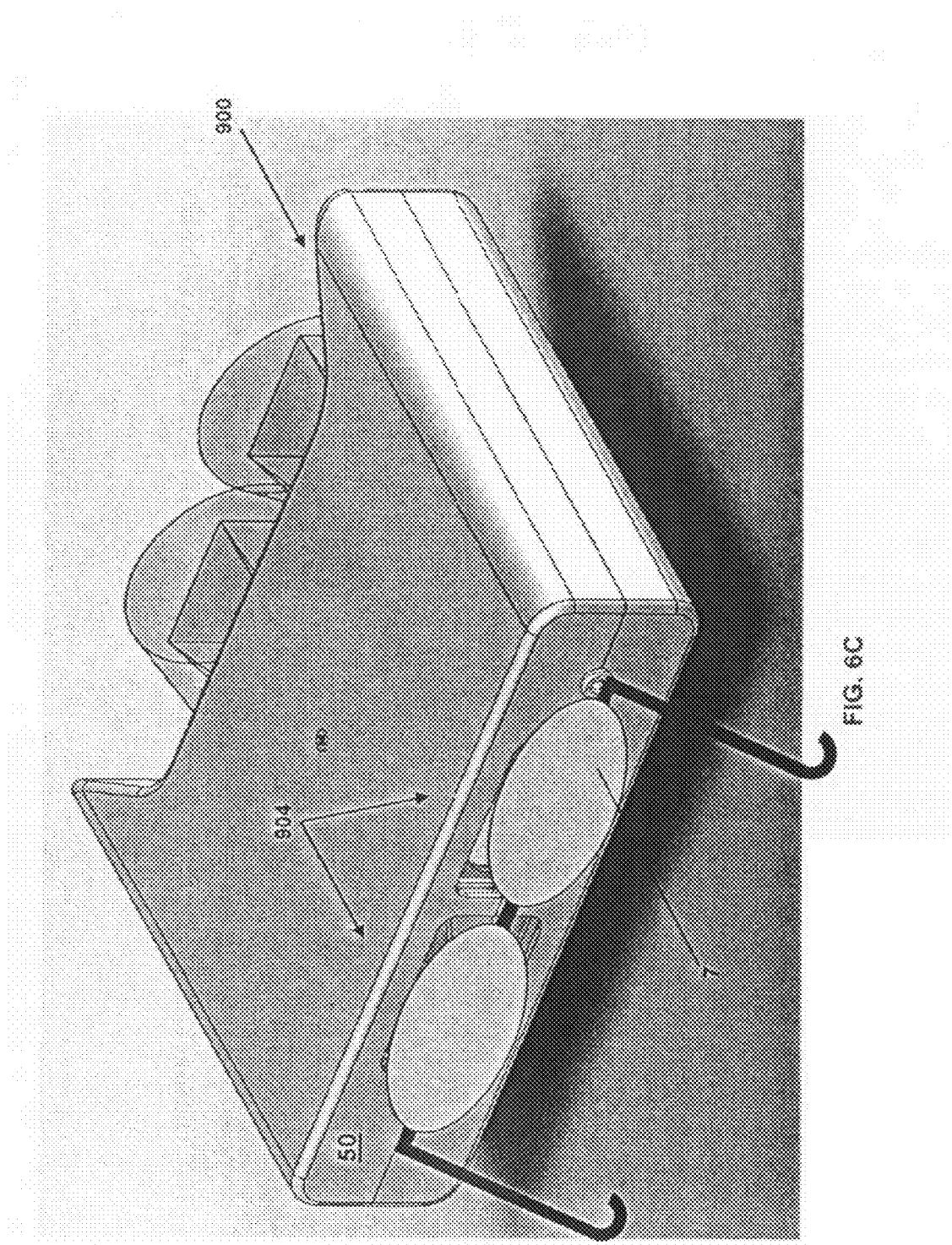

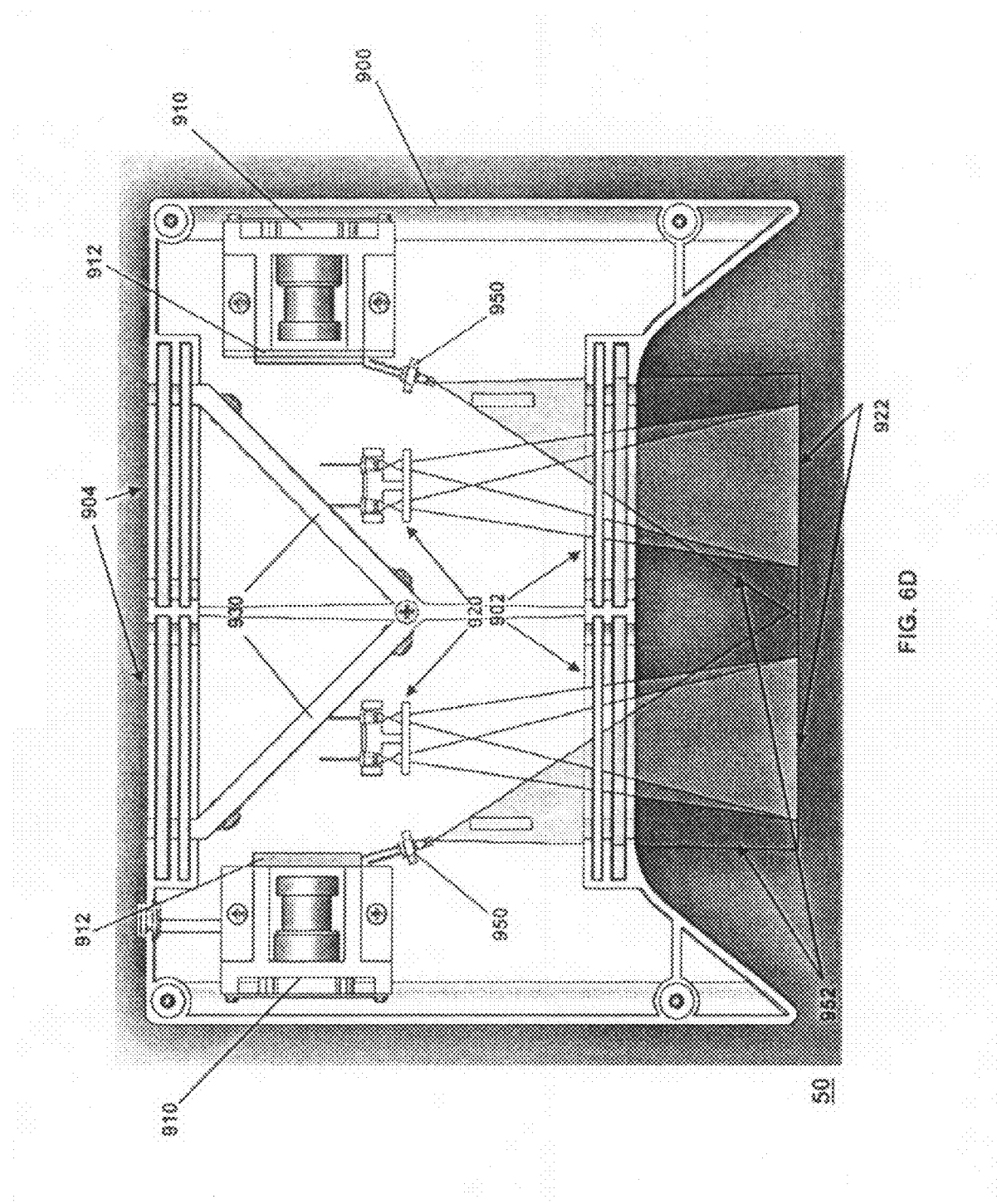

ALIGNED IN X, Y, Z

MISALIGNED IN Z

MISALIGNED IN X, Y, Z

MULTIMODAL OCULAR BIOMETRIC SYSTEM

CROSS REFERENCE TO RELATED APPLICATIONS

This application claims priority to U.S. Provisional Application No. 60/800,023 filed May 15, 2006, U.S. Provisional Application No. 60/812,949 filed Jun. 13, 2006, and U.S. Provisional Application No. 60/819,630 filed Jul. 11, 2006, the contents of these applications being incorporated entirely herein by reference.

BACKGROUND OF INVENTION

1. Field of Invention

The present invention relates generally to instruments for biometric identification, and more particularly, to a multimodal ocular imaging system used for biometric identification.

2. Description of the Related Art

Due to the unique character of each individual's retina or iris, various systems attempt to use either the retina or the iris for biometric identification. As such, commercially available ocular imaging systems used for biometric identification generally use a single biometric modality. These imaging systems process images of the iris or the retina from only one of two eyes of a subject. None of these conventional systems processes images of both the iris and the retina in combination. Moreover, these systems do not process images from the iris and/or the retina from both eyes.

Conventional single-eye iris imaging systems suffer from several disadvantages. In particular, such systems may suffer from frequent failure to acquire an image, i.e. a high fail-to-acquire (FTA). The effectiveness of these iris imaging systems is often limited by occlusions caused by eyelids and eyelashes, lighting issues (controlled or uncontrolled), focus problems, pupil size variation (between different persons or with the same person), non-linear iris fiber distortion caused by expansion or contraction of the pupil, and rotation and skew of the head or eye. Such systems are also susceptible to spoofing. Moreover, auto focus functions of conventional iris-only systems are affected by scratches in eyeglasses or the reflections from eyeglasses. In fact, ANSI standards require enrollment to be without eyeglasses. Additionally, contact lenses can cause iris outer boundary segmentation problems. Moreover, colored contact lenses can result in spoofing.

Conventional single-eye retina imaging systems also have several disadvantages. For instance, problems with such retina imaging systems occur when visible light used for illumination blinds or distracts the user, when the user is not properly aligned with the image capture device, or when poor areas of the retina are chosen for imaging. Furthermore, conventional retina-only systems are also negatively affected by focus problems as well as rotation and skew of the head or eye.

SUMMARY OF THE INVENTION

Considering the disadvantages of the single modal systems described previously, a need has been identified for a multimodal ocular biometric system that addresses these disadvantages by capturing and combining biometric information from more than one modality.

Accordingly, embodiments of the present invention provide a multimodal ocular biometric system that captures and processes images of both the iris and the retina for biometric identification. Biometrics based on a combination of iris and retina data provided by the present invention are more accurate and robust than using biometrics that include data from only the iris or only the retina from a single eye. In addition, such a multimodal system has a lower fail-to-acquire (FTA) than single-eye iris-only or retina-only systems and is less susceptible to spoofing. It is noted that U.S. application Ser. No. 11/087,205, filed on Mar. 25, 2005, describes a Method and System for Generating a Combined Retinal/Iris Pattern Biometric, and is entirely incorporated herein by reference.

Thus, in an exemplary embodiment of the present invention, a system for multimodal biometric identification has at least one iris imaging system and at least one retina imaging system. Each iris imaging system has an iris illumination source adapted to emit iris photons to an iris of a right eye or a left eye and an iris image sensor configured to capture an image of the iris when the iris reflects the iris photons, where the image of the iris having iris biometric data. Each retina imaging system has a retina illumination source adapted to emit retina photons to a retina of the right eye or the left eye and a retina image sensor configured to capture an image of the retina when the retina reflects the retina photons, where the image of the retina having retinal biometric data. The exemplary embodiment employs a controller adapted to control the at least one iris imaging system and the at least one retina imaging system. The iris image sensor of the at least one iris imaging system captures the image of the iris according to operation of the corresponding iris illumination source, and the retina image sensor of the at least one iris imaging system captures the image of the retina according to operation of the corresponding retina illumination source.

Other embodiments of the present invention provide a multimodal ocular biometric system that captures and processes images of the iris and/or the retina from both eyes. Biometrics based on data from both eyes are also more accurate and robust than using biometrics that include data from only the iris or only the retina from a single eye. For example, in another exemplary embodiment, a system for multimodal biometric identification employs a binocular-shaped image capture device that allows a user to look through the device to view an object external to the device with both eyes, while the iris of each eye is illuminated and an image of each iris is captured by an image sensor.

Embodiments may use different combinations and configurations of iris illumination sources, retina illumination sources, iris image sensors, and retina image sensors to capture data from more than one modality. For example, images of the iris and the retina of both eyes may be captured and processed. Meanwhile, yet further embodiments may employ varying techniques for illuminating the iris or the retina, tracking the position of the iris or the retina, and achieving the best possible images of the iris or retina. For example, the tracking of the iris (or retina) may be employed to capture the best possible image of the corresponding retina (or iris).

Still other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE FIGURES

FIG. 3 illustrates an embodiment of the present invention with a dual-sensor, two-eye flippable configuration.

FIG. 4 illustrates an embodiment of the present invention with a triple-sensor, two-eye sequential configuration.

FIG. 6B illustrates another external view of the embodiment of FIG. 6A.

FIG. 6C illustrates the use of corrective eyewear with the embodiment of FIG. 6A.

FIG. 6D illustrates an internal view of the embodiment of FIG. 6A.

DETAILED DESCRIPTION

Embodiments of the present invention provide a multimodal ocular biometric system that captures and processes images of both the iris and the retina, from which data can be determined for biometric identification. Further embodiments provide a multimodal ocular system that captures and processes images of the iris and/or the retina from both eyes of a subject. Biometrics based on data provided by these embodiments are more accurate and robust than using biometrics that include data from only the iris or only the retina from a single eye.

Advantageously, the iris and retina present biometric features that are both independent and strongly coupled. They are independent in that they are extracted from different biological structures. On the other hand, the iris and retina biometric features are strongly coupled because there is a fixed geometric relationship between the iris and the retina. Specifically, the position and orientation of the eye is reflected simultaneously in both the iris and the retina. Further, the biometric features of the iris and the retina are on the same scale. The strong coupling between the biometric features of the iris and the retina not only facilitates the simultaneous capture of these biometric features, but allows these features to be cross-referenced or combined in a common feature space that preserves the geometric relationship between the iris and retina. In addition, the use of an iris system complements the use of a retina system. For instance, small pupils are generally an advantage for iris systems while large pupils are generally an advantage for retina systems.

Figure 1:
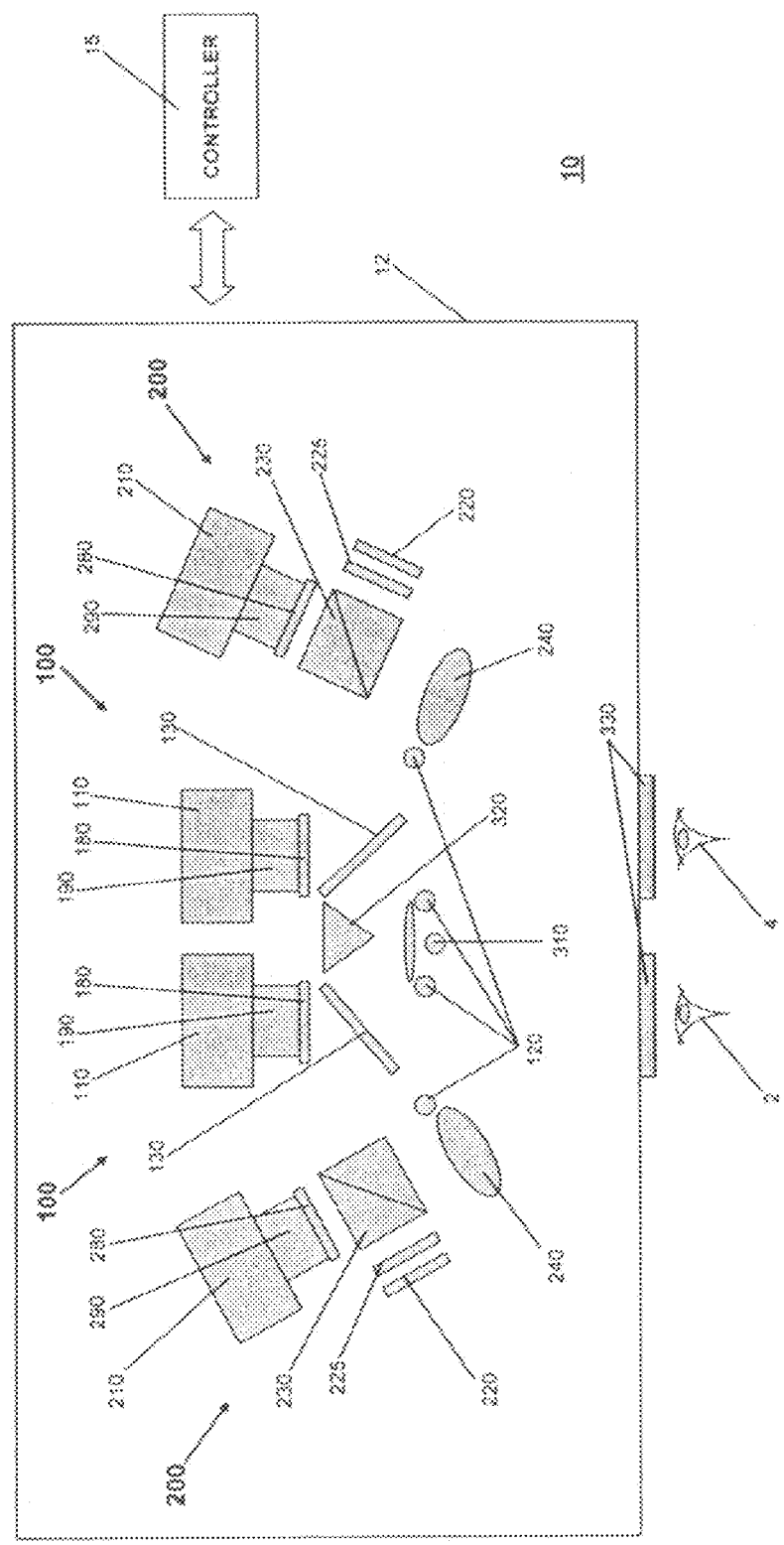
FIG. 1 illustrates an embodiment of the present invention with a quadruple-sensor, two-eye simultaneous configuration.

Accordingly, embodiments of the present invention employ various configurations of at least one imaging system that captures iris images and retina images. For example, FIG. 1 illustrates a two-eye simultaneous iris/retina combination system, which employs two iris imaging systems that respectively capture iris images of the right and left eyes, and two retinal imaging systems that respectively capture the images of the right and left retina, all simultaneously, or at least substantially simultaneously. Information from the imaging systems is used to accomplish retinal pattern recognition, iris pattern recognition, and biometric fusion. Moreover, the information from the individual imaging systems are used in combination to establish a host of attributes including, but not limited to, positioning, tracking, focus, and interpupillary distance. In addition, the multimodal ocular biometric system is especially well suited for image capture of both eyes when the user is not wearing corrective eyewear. Although many of the features of the present invention may be described with respect to the two-eye simultaneous iris/retina combination system shown in FIG. 1, other configurations, as described further below, can implement these features in order to combine iris and retina images for biometric identification.

Referring to FIG. 1, the multimodal ocular biometric system 10 includes an optical system which is symmetric for both the left eye 2 and the right eye 4. The multimodal ocular biometric system 10 includes two camera sensors 110 to capture respective images of the iris in the right and left eyes. The system 10 also has two camera sensors 210 to capture respective images of the retina in the right and left eyes. As such, an iris imaging system 100 and a retina imaging system 200 are provided for each eye. Therefore, iris and retina images can be captured simultaneously, or at least substantially simultaneously. Preferably, the iris imaging systems 100 and the retina imaging system 200 are housed in a single image capture device 12, as depicted in FIG. 1.

The biometric information collected from the system 10 includes iris patterns and retina patterns, from which biometric data can be extracted. Liveness detection, which detects whether the biometric information comes from a living source, may also be achieved with the system 10. U.S. patent application Ser. No. 11/258,749, filed on Oct. 26, 2005, describes a Method and System for Detecting Biometric Liveness, and is entirely incorporated herein by reference.

Furthermore, as described in more detail below, by capturing images of both irises simultaneously, the system 10 is able to provide biometrics, such as interpupillary distance and limbus diameter for both the right and left eyes. Advantageously, measurements of the interpupillary distance and limbus diameter can be used to improve database searching during biometric identification, because they allow reference data to be binned and narrowed to a relevant subset of data before a search is conducted for matches based on iris codes or retinal codes. In this way, a comprehensive search of all reference data for biometric matching is not required. For instance, limbus diameters for the general population have a range of about 9.5 mm to 13.5 mm. Thus, if the system 10 measures a limbus diameter to be 10.5 mm, a subset of reference data covering individuals with limbus diameters in a range of 10.25-10.75 mm, rather than the entire database, may be searched. Compared to conducting a comprehensive search, the time to obtain a match with the reference data may improve by up to 8 times when narrowing the data down according to ranges of limbus diameter in this manner. Moreover, interpupillary distances for the general population have a range of ±10 mm. Obtaining a ±1 mm resolution would thus improve search times by up to a factor of 10. As a result, narrowing the search data according to limbus diameter and the interpupillary distance may improve search times by 80 (8×10), which may be significant for very large databases. Also, throughput can be enhanced by system memory caching based on bins for mid-sized databases in multi-machine systems. Considering N interpupillary distance bins, if N machines with N local system memories each have enough system memory to hold the entire bin for an interpupillary distance in the database, then database access is less likely to become a system bottleneck.

To capture the iris and retina images, the multimodal ocular biometric system of the present invention employs both iris illumination adapted to emit photons to the iris of an eye and retina illumination adapted to emit photons to the retina of the eye. In particular, the embodiment shown in FIG. 1 employs LEDs (light emitting diodes) 120 and 220 to produce iris illumination and retina illumination, respectively. FIG. 1 also shows that the iris and retina illumination uses separate LED's. Correspondingly, the camera sensors 110 are configured to capture iris images when the right and left irises reflect the emitted light from the illumination source 120, and the camera sensors 210 are configured to capture retina images when the right and left retinas reflect the emitted light from the illumination source 220.

Alternatively, other embodiments of the present invention may employ laser diodes rather than LEDs. In these alternative embodiments, the system can perform laser Doppler imaging using an addressable CMOS detector on specific regions of interest. Advantageously, this approach permits retinal liveness testing as well as retina vessel determination and contrast enhancement.

As depicted in FIG. 1, a controller 15 is operably connected to the iris illumination and the retina illumination, such as LED's 120 and 220. The controller 15 manages the manner in which the iris illumination and the retina illumination emits photons to the irises or the retinas, respectively. As is known, the controller 15 may be a programmable processing device that executes software, or stored instructions. For example, the controller 15 may employ an external conventional computer networked with the image capture device 12. Alternatively, a field programmable gate array (FPGA) or digital signal processor (DSP) may be employed on board the image capture device 12. In general, the systems described herein may employ a controller, as well as other processors, that are either internal or external to the image capture devices, which house the illumination and sensor systems.

The wavelengths for illumination of the iris and retina may be in the near infrared (NIR) (700 nm to 1000 nm). Special filters or coated optics may be used in the optical train to select specific wavelengths to satisfy the 700 nm to 900 nm wavelength requirements for the ANSI specification for Iris Image Interchange Format (ANSI INCITS 379-2004), but still allow a visible color image.

Accordingly, in the exemplary embodiment illustrated in FIG. 1, the iris illumination system of the present invention may operate to illuminate just the inner orbit of the eye. Preferably, the area of interest outside the field of view (FOV) of the iris camera 110 is not over-illuminated, as illumination outside the FOV can cause reflections off the cheek, forehead, or nose creating non-uniform illumination of the iris. This is especially the case for people who wear makeup containing $TiO_2$. Moreover, illuminating the area outside the FOV of the camera is a waste of light and energy. Two arrays of LEDs 120 at a wavelength of 850 nm, for example, are masked and focused on the iris and sclera in order to create this uniform illumination. The illumination occurs at an angle of approximately ±15 degrees measured from the line of sight of the user in order to minimize retro-reflection off the retina with the associated bright pupil corresponding to the iris image. The pupil must remain dark for image analysis and to meet ANSI INCITS specification.

Light reflecting off the iris passes through a broadband antireflection coated optical window 330 and is imaged back through the imaging system, through a dichroic beamsplitter 130. The light then passes through a plastic or glass longpass filter 180 with a cutoff wavelength of 780 nm, for example. The longpass filter 180 prevents ambient visible light from entering the imaging system and creating noise in the image. The light is then focused with the iris imaging lens 190 to the image sensor 110. In a particular embodiment, the sensor 110 is a CMOS (complementary metal-oxide semiconductor) detector with high sensitivity to NIR illumination. The CMOS detector may have square pixels, a wide angle format, and a global shutter.

In general, the iris imaging system of the present invention may have a refractive lens (a single or a series of lenses) 190 which images the iris to a CMOS image sensor 110 or, alternatively, a CCD (charge-coupled device) sensor 110. The image capture device 12 may also employ reflective or a combination of refractive and reflection optics. The imaging sensor 110 may also have a global shutter or a rolling shutter.

In addition, embodiments may include an iris imaging system which uses digital processing algorithms for pupil tracking and iris focus measurement. For example, a pupil tracking algorithm may employ segmentation, e.g. a caliper technique, to determine pupil position. Meanwhile, an example of an algorithm for iris focus measurement is disclosed in application Ser. No. 11/526,096, filed on Sep. 25, 2006, which is entirely incorporated herein by reference. With these two features, the three dimensional position of the iris with respect to the device 12 is determined for both left and right eyes. For example, information regarding position along X- and Y-axes may be determined from the pupil tracking and information regarding position along the Z-axis may be determined from the iris focus measurement. Evaluation of this position data may determine when images of acceptable quality have been captured and should be utilized for biometric data.

As further illustrated in FIG. 1, the retina illumination may employ a tracking system to illuminate the optic nerve head of the retina. For instance, arrays of LED's 220 at a wavelength of 880 nm spaced 1 mm apart are aligned to 1 mm diameter and 10 mm long hollow tubes. The hollow tubes create a homogenizing waveguide for the light emanating from them. Only a single element of the array is illuminated at a time corresponding to the determination of the pupil's position in space, as determined by the digital processing algorithms, including segmentation and focus measure. As such, analysis of the iris image yields pupillary positional information that may be employed to determine illumination of the corresponding retina. In other words, the pupil's position is used to determine which LED 220 in the array aligns most optimally with the retina and should be activated for illumination of the retina. Reference numeral 225 in FIG. 1 illustrates a diffuser, which is placed over the ends of the tubes to create a 1 mm spot from the active LED 220.

Alternatively, reference numeral 225 may refer to an LCD shutter, which can create a similar 2-dimensional series of singly activated illuminators that are 1 mm in diameter and imaged to the eye. Depending on the determination of the pupil's position in space, the LCD shutter 225 allows light from the illumination source 220 to pass through an appropriate section of the LCD device 225 to illuminate the retina. As further alternatives, scanning micro-optics or holographic elements may also be employed.

The light from the LCD shutter/diffuser/micro-optics 225 reflects off a polarizing beamsplitter (PBS) 230 creating S polarized light. This light is then imaged by the aspheric objective lens 240, through a long pass plastic sheet filter with a 780 nm cutoff wavelength, to a 2 mm spot just before the nominal position of the cornea. The angle of the light entering the pupil is nominally 15.5 degrees temporal to and 1.5 degrees inferior to the line of sight of the user. The spot diameter is chosen to be smaller than the pupil so that light does not scatter off its edges causing excess noise in the retina image. The divergence of the light is approximately 10 degrees half angle. This allows for imaging of a large enough FOV to obtain a suitable retina image for pattern recognition. The retina image consists of the blood vessel pattern emanating from the optic nerve head. Absorption of the light by hemoglobin and oxyhemoglobin in the blood creates the outline of the blood vessel pattern. Demarcation of the optic nerve head may or may not be discernable. The LED's have three pulse duration settings that are cycled through (exposure bracketing) so as to accommodate for reflectance differences of the retina in the general population.

Light reflecting off the retina passes back through the long pass cutoff filter. This filter prevents ambient visible light from entering the imaging system and creating noise in the image. It also hides the imaging optics from the user. The light is then collected by the aspheric objective lens 240 to produce a real image just before the polarizing beamsplitter 230. This real image is then imaged though the PBS 230 allowing only P polarized light to pass. The purpose of the PBS 230 is to increase the signal to noise ratio of the signal by rejecting any S polarized light reflected back through the system from other optical surfaces. An imaging lens followed by a cubic phase mask optic then images the light onto a camera sensor 210. The camera sensor 210 may be a CMOS detector with high sensitivity to NIR illumination. The CMOS detector has square pixels, has a wide angle format, and has a global shutter.

The images of the retina are multiplied by specific digital filters. These filters are created for differences in dioptric power correction. The images are evaluated using a retina focus measure algorithm and the one with the highest contrast image is preferably utilized for biometric identification. An example of a retinal focus measure algorithm is described in application Ser. No. 11/785,924, filed Apr. 20, 2007, which is entirely incorporated herein by reference.

The illumination for the iris may have a different wavelength from the illumination for the retina. In one embodiment of the present invention, the retina is illuminated with light of a first wavelength, the light of the first wavelength being reflected from the retina to the retina image capturing device. The iris is illuminated with light of a second wavelength that is different from the first wavelength, the light of the second wavelength being reflected from the iris to the iris image capturing device. The first wavelength of light is selected to provide enhanced contrast between biometric features of the retina, such as a retinal vessel pattern, and the background in the captured image. Similarly, the second wavelength of light is selected to provide enhanced contrast for the biometric features of the iris.

If the iris illumination and the retina illumination occur at the same time or in near time, however, the iris illumination can introduce noise in the retina signal, or vice versa. To avoid introduction of noise between the illumination of the iris and retina, dichroic optics can be employed to allow wavelength separation from the different illumination sources, where light of one wavelength is directed to one sensor while light of a second wavelength is directed to another sensor. The illumination with special dichroic optics can be pulsed or run as a continuous wave.

More advantageously, to eliminate the introduction of noise between the illumination of the iris and retina, the iris illumination and the retina illumination can be separated by pulsing the individual LEDs with a synchronized offset. For instance, the iris and retina cameras can run at 30 frames per second offset by half a frame (16.5 ms) with a shutter (global, rolling or global-rolling hybrid) of 10 ms. The pulses from the LEDs occur at 10 ms so that neither camera sees light from the other illumination LEDs. The advantage of pulsing illumination with a synchronous offset is that it freezes motion, maximizes frame rate without having to use dichroics, and allows higher pulse energies which reduces gain on the camera, thereby increasing image quality. Furthermore, pulsing illumination with a synchronous offset permits the use of the same wavelength for the illumination of the iris and retina.

In general, both iris and retina illumination may use auto gain in order to correct for the proper exposure for correction of reflectance differences of the iris and retina. Alternatively, both iris and retina illumination bracketing (or exposure bracketing) may be used instead of auto gain. In this alternative approach, two or more illumination power settings are cycled through to bracket through all possible reflectance differences seen in the general population; for example: power setting 1 (pulse 1)=10 units, power setting 2 (pulse 2)=12 units, power setting 3 (pulse 3)=14 units, where cycle=pulse 1, pulse 2, pulse 3, pulse 1, pulse 2, pulse 3, . . . an so on. One could also do this by keeping the power constant and cycling three different pulse durations; for example: pulse duration 1 (pulse 1)=10 units, pulse duration 2 (pulse 2)=12 units, pulse duration 3 (pulse 3)=14 units, where cycle=pulse 1, pulse 2, pulse 3, pulse 1, pulse 2, pulse 3, . . . an so on.

Accordingly, in the embodiment shown in FIG. 1, the iris illumination can advantageously be pulsed at less than half the frame rate of the iris and retina cameras. The frame rates for both cameras are identical. The image of the iris is analyzed with the pupil tracking and iris focus measure digital processing algorithms. The $X_1$, $Y_1$, and $Z_1$ positions of the pupil of the iris are calculated. The user must move through the nominal $Z_N$ position of the system which establishes the absolute position of the user. Until that time, the system assumes a relative position of the pupil based on pupil size. Iris images that are adequately in focus are collected and analyzed appropriately. As described above, the LED's have three power settings that are cycled through (exposure bracketing) so as to accommodate for reflectance differences of the iris in the general population.

As described previously, the positional information of the pupil is utilized to select the addressable retinal illumination LED that will cleanly enter the pupil. The retina illumination LED is pulsed at half a frame out of phase from the iris illumination. The pulse duration is less than half the frame rate. As described above, by synchronizing the iris and retinal frame rates of the camera at half a frame rate out of phase with each other and using short pulses, the full frame rate of each camera can be utilized while minimizing noise that may occur between the illumination of the iris and the retina. Illumination pulses with shorter time frames freeze motion and increase image quality.

The present invention may also employ a retina auto focus mechanism, which corrects for changes in retinal focus due to differences in uncorrected dioptric power and allows any corrective optical devices to be removed by the user. Corrective optical devices can cause aberrations and glare. Several techniques may be applied to achieve retina auto focus.

Figure 2A:
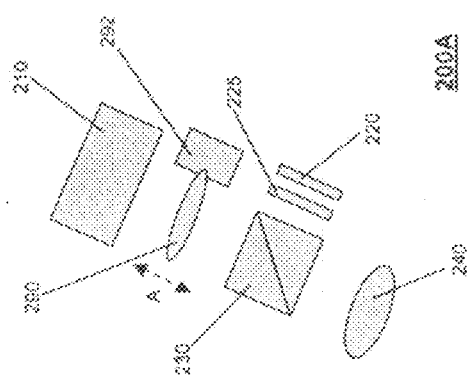
FIG. 2A illustrates a retina auto-focus technique employed by an embodiment of the present invention.

As shown in the retina imaging system 200 of FIG. 2A, one technique for retina auto focus employs a motor 292 that moves the focus of the retina imaging lens 290 in specific dioptric value increments, along the arrow A as shown in FIG. 2A. The system utilizes a retina focus measure algorithm comparing successive positions. If the system remains out of focus, the system uses this comparison to determine the direction in which it should move.

Figure 2B:
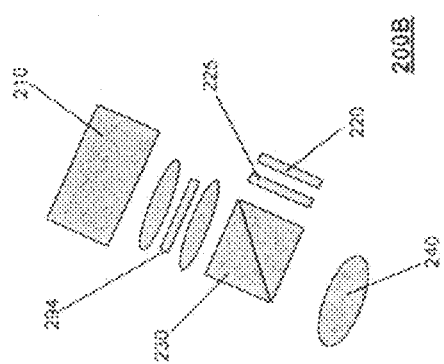
FIG. 2B illustrates another retina auto-focus technique employed by an embodiment of the present invention.

As shown in FIG. 2B, another technique for retina auto focus employs wavefront coding technology using cubic phase plate and signal analysis. FIG. 2B illustrates a retina imaging system 200B with an imaging lens with a cubic phase plate, indicated by reference numeral 294. Contrary to the use of the motorized lens, there are no moving parts with wavefront coding. A cubic phase mask is placed in the system and the system is fully characterized with regard to dioptric power correction. Differences in dioptric power correction are calculated and specific digital filters are created for each dioptric power. When an image is taken, each of the filters is convolved with the image and the one with the highest contrast image is utilized. This configuration provides a robust system, which can be used at extreme temperatures, because there are no moving parts.

Figure 2C:
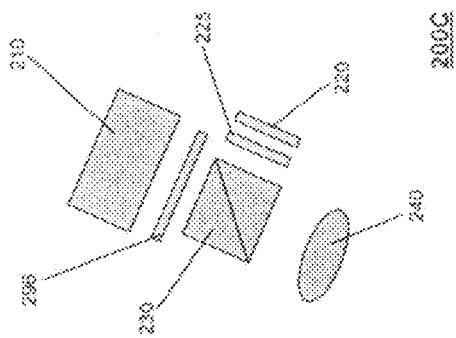
FIG. 2C illustrates yet another retina auto-focus technique employed by an embodiment of the present invention.

As depicted in the retina imaging system 200C of FIG. 2C, a third technique for retina auto focus uses an electroactive optical element 296, which is a liquid crystal sandwiched between two pieces of glass with a specific electrode configuration on them. By activating the electrodes with different voltages, either a positive or negative dioptric correction may be created. This can be a single device or a stack of devices to create larger dioptric correction.

While the auto focus systems above have been described in terms of retina imaging, it is understood that such auto focus techniques are also applicable to an iris auto focus system.

In general operation, the multimodal ocular biometric system according to the present invention may be handheld, but may also be attached to an articulating arm, attached to or embedded into an immovable object such as a wall, or adapted to an existing optical system such as a rifle scope or tank periscope. As described further below, the system may possess a simple fixation system, or interface, to position the user. For instance, with an exemplary handheld embodiment, the user picks up the device and removes any eyeglasses the user may be wearing. The user then identifies a fixation illumination source within the device and carefully positions the device with respect to his or her face according to the fixation illumination source. As also described in another embodiment below, the outer housing of the device may be designed to help center the user as well as to provide light baffling of external ambient light.

Figure 7:
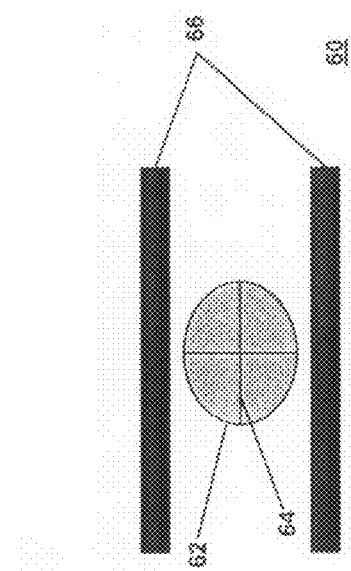
FIG. 7 illustrates an exemplary fixation scheme as seen by the user.

With reference to FIG. 1, the user operates the image capture device 12 by identifying the fixation light source 310 through the broadband antireflection coated windows 330. The light from the source 310 reflects off the beamsplitter and cold mirror 320. In a fixation system 60 illustrated in FIG. 7, a circular target 62 with cross hairs 64 is viewed through an imaging lens with two illuminated bars 66 above and below the lens. The illuminated bars 66 are positioned at the exit pupil of the device 12. The bars 66 may include a diffusing light guide with colored LEDs illuminating them. The circular target 62 is a reticule with a diffuser and colored LEDs behind it. The user operates the fixation system 60 by moving the device 12 relative to his or her eyes to center the circle 62 between the two bars 64. As the user moves back and forth relative to the device 12, different colored combinations may help guide his or her movement.

The image capture device 12 may also employ provide positional feedback to the user by using the pupil tracking and iris focus measure digital processing algorithms. A retina focus measure digital processing algorithm can be used in place of, or in combination with, an iris focus measure digital processing algorithm.

Figure 8C:
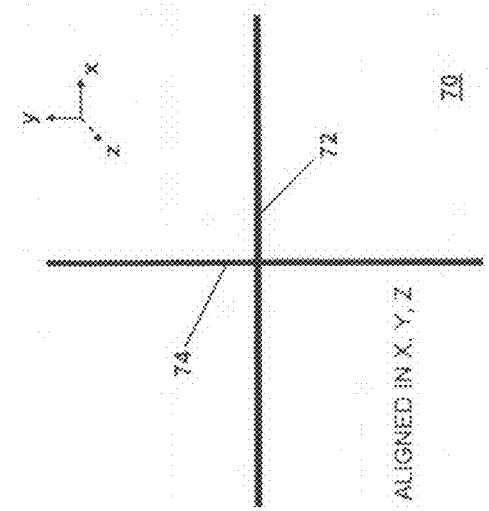
FIG. 8C illustrates another exemplary fixation scheme, as seen by the user when the user is aligned along the X-, Y-, and Z-axes.
Figure 8B:
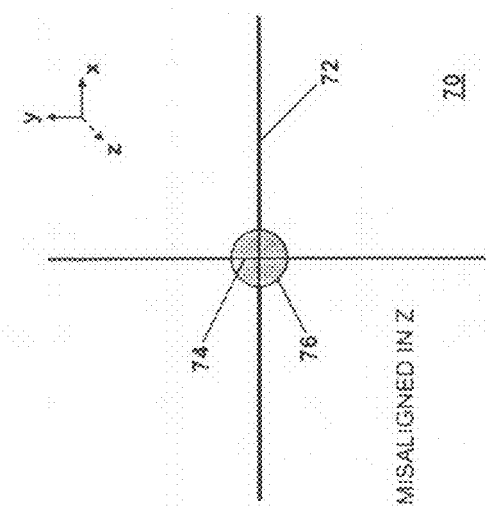
FIG. 8B illustrates another exemplary fixation scheme, as seen by the user, when the user is misaligned along the Z-axis.
Figure 8A:
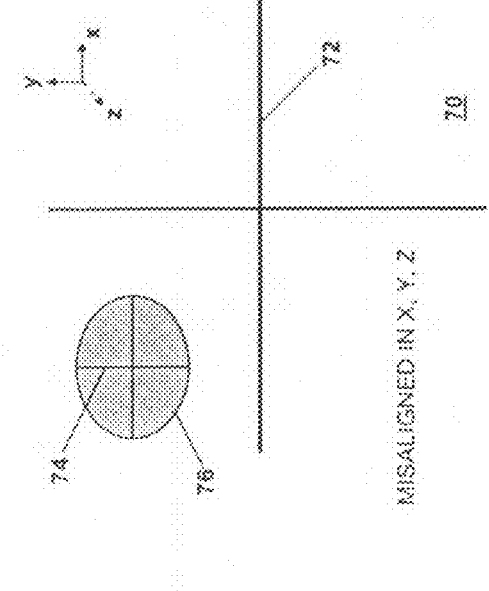
FIG. 8A illustrates another exemplary fixation scheme, as seen by the user when the user is misaligned along the X-, Y-, and Z-axes.

In another fixation system 70 illustrated in FIGS. 8A-C, an interface provides a set of central cross hairs 72 designating nominal positioning ($X_N, Y_N, Z_N$) for optimal alignment by the user relative to the device 12 and a second set of cross hairs 74 with a circle 76 designating the user's present position ($X_1$, $Y_1, Z_1$). When the user moves along the X- and Y-axes (left, right, up and down as shown in FIGS. 8A-C), the cross hairs 74 with the circle 76 correspondingly move along the X- and Y-axes. When the user moves back and forth relative to the device along the Z-axis the diameter of the circle 76 becomes larger as the user moves away from the nominal $Z_N$ position and smaller as the user moves towards the nominal $Z_N$ position. When the circle 76 disappears, the user is positioned at the nominal $Z_N$ position. Furthermore, when the user sees only a single set of cross hairs, the second set of cross hairs 74 overlaps with the central cross hairs 72. Therefore, the image of FIG. 8A indicates that the user is misaligned along the X-, Y-, and Z-axes. Meanwhile, the image of FIG. 8B indicates that the user is aligned along the X- and Y-axes, but misaligned along the Z-axis. When the interface shows the image of FIG. 8C, the user has achieved the nominal position ($X_N$, $Y_N, Z_N$). Auditory feedback may be additionally employed with the fixation system 70, signaling the user with appropriate tones and/or verbal instructions to move the user into optimal alignment.

Figure 9:
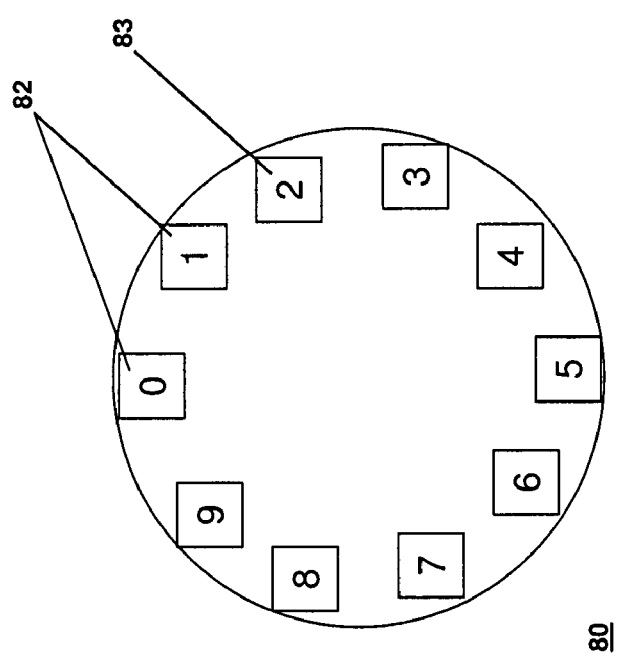
FIG. 9 illustrates an exemplary scheme for entering a personal identification number by pupil tracking.

As shown in FIG. 9, embodiments of the present invention may include, in combination with the fixation system, a clock interface 80 that accepts a pin number for further identification. When users look into the device, they begin by looking at a start position. They then enter their pin number by fixating on the numbers or other symbols 82. The system uses the pupil tracking to determine the trajectory of the different pupil positions to identify each number or symbol 82 entered by the user. Verification of each number or symbol 82 can be indicated through aural tones and/or visible color changes, as illustrated by number 83 in FIG. 9.

In addition to the two-eye simultaneous iris/retina combination system shown in FIG. 1, other configurations can be employed to combine iris and retina images. A left-eye only configuration employs iris and retina imaging systems to capture images of the left eye only. Similarly, a right-eye only configuration employs iris and retina imaging systems to capture images of the right eye only.

As shown in FIG. 3, a dual sensor, two-eye "flippable" system 20 provides one iris imaging system 400 and one retina imaging system 500 in an image capture device 22 that can be oriented to capture images of both the left and right eyes, in succession. In particular, the same iris imaging system 400 and retina imaging system 500 are used to capture images of the left and right eyes. Once images of one eye are captured, the user flips, or turns the device over, to capture images of the second eye. Flipping the device over maintains the correct orientation of the iris and retina imaging systems with respect to the eye. For example, the specific orientation shown in FIG. 2 permits the capture of images from the right eye 4.

Similar to the iris imaging system 100 described previously, the iris imaging system 400 in FIG. 3 employs a camera sensor 410 which captures images of the illuminated iris through a dichroic beamsplitter 430. Similar to the retina imaging system 200 described previously, the retina imaging system 500 in FIG. 3 employs an illumination source 520 that provides light that is guided through a LCD shutter/diffuser/micro-optics 525, a polarizing beamsplitter (PBS) 530, and an aspheric objective lens 540 to the retina. Furthermore, the image of the retina then passes back through the aspheric objective lens 540 and the PBS 530 to the camera sensor 510. The system 20, however, employs a dual fixation LED with orientation sensor 525, where one of the two LED's is activated according to the "flipped" orientation of the device 22. An orientation sensor senses the orientation of the device 22 and correspondingly turns on the appropriate fixation LED.

Moreover, the system 20 as shown in FIG. 3 also uses a dual retina/iris illumination and retina illumination tracking configuration. In other words, the illumination source 520 provides illumination of the iris as well as the retina. The retina illumination system in this embodiment is similar to the illumination system for the retina in the two-eye simultaneous system 10 shown in FIG. 1, where the element of the LED array is illuminated according to the pupil's position in space. The captured iris image is used to track the position of the pupil in order to identify the specific LED that should be used to provide the necessary pinpoint illumination of the retina in the subsequent image capture. Here, however, both the retina illumination and iris illumination emanate through the retina imaging optics. The addressable light source array 520 is used to create pulsed light for both iris and retina illumination. All elements in the array 520 are employed to illuminate the iris. Then, using the pupil tracking digital processing algorithm and iris focus measure digital processing algorithm, selected elements in the array are turned on to illuminate the retina. As the position of the iris moves the appropriate elements in the array are selected for both the retina and iris. For the retina illumination, the illumination elements of the array imaged (to just before the retina) are smaller than the pupil of the iris. Advantageously, this illumination configuration enables simplification of the packaging, minimizes reflections off the orbit of the eye for uniform iris illumination, and allows scanning of the retina for increased volume of alignment. As described above, the addressable light source array can be built in several different configurations, including, but not limited to, the use of an LED array with light guides and diffuser and an LCD shutter, scanning micro-optics, and holographic elements, as indicated by reference numeral 525.

In another embodiment illustrated in FIG. 4, a triple sensor, two-eye sequential system 30 employs one iris imaging system 600 and two retina imaging systems 700 in device 32 to capture sequential, or successive, images of both the left and right eyes. The same iris imaging system 600 is used to image the iris of both the left and right eyes, while two retina imaging systems 700 with specific left and right orientations are used to image the left and right eyes, respectively. Unlike the two-eye flippable system 20, the system 30 of FIG. 4 does not have to be flipped, or turned over, to capture images of the second eye. Thus, it easier to reposition for capture of images from the second eye, because the same horizontal plane can be maintained. In addition, a dual fixation LED with orientation sensor does not have to be employed. Rather, a single fixation source 310 may be employed.

Similar to the iris imaging system 100 described previously, the iris imaging system 600 in FIG. 4 employs a camera sensor 610 which captures images of the illuminated iris through a dichroic beamsplitter 630. Similar to the retina imaging system 200 described previously, the retina imaging system 700 in FIG. 4 employs an illumination source 720 that provides light that is guided through a LCD shutter/diffuser/micro-optics 725, a polarizing beamsplitter (PBS) 730, and an aspheric objective lens 740 to the retina. Furthermore, the image of the retina then passes back through the aspheric objective lens 740 and the PBS 730 to the camera sensor 710.

Figure 5:
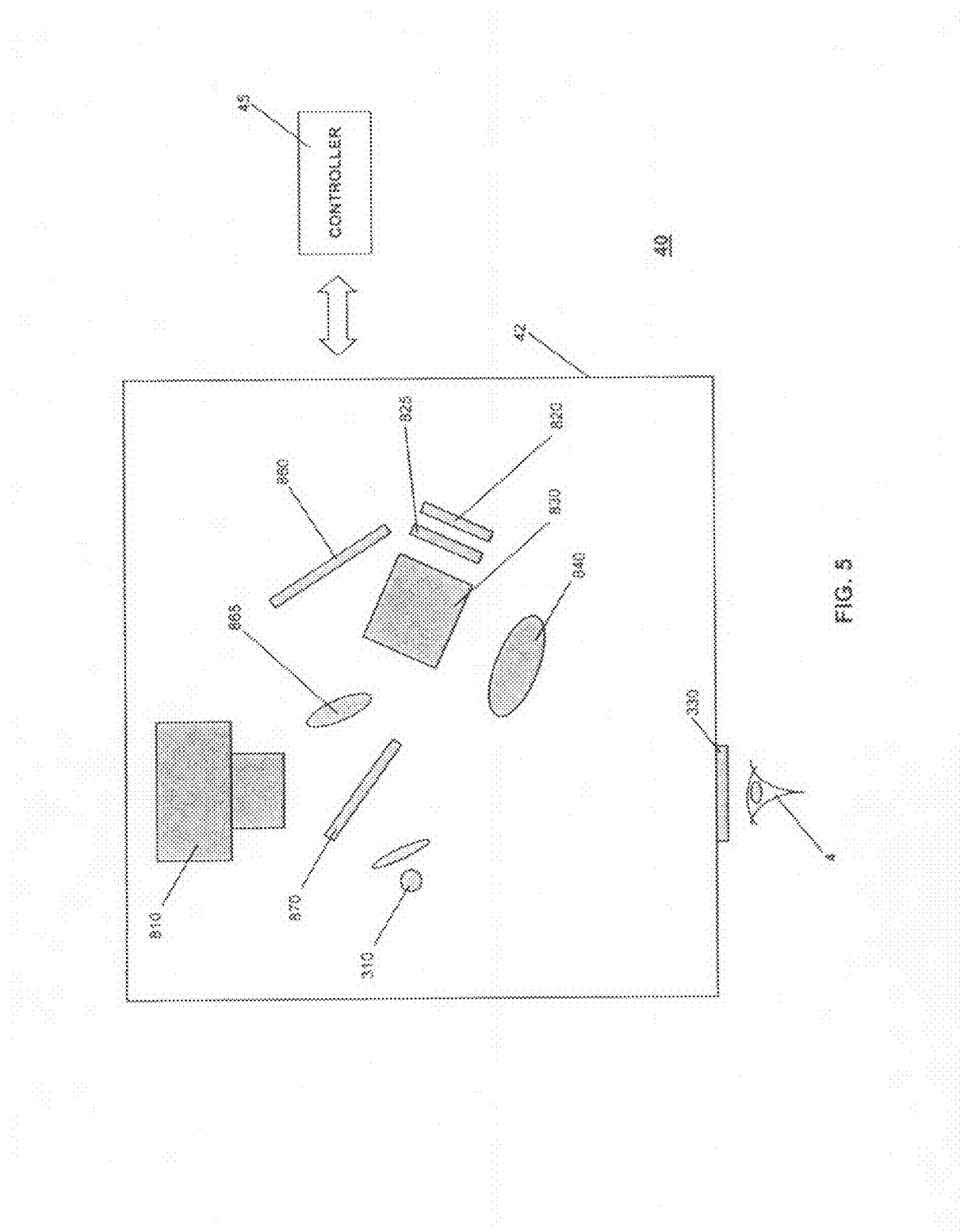
FIG. 5 illustrates an embodiment of the present invention with a single-sensor, two-eye sequential configuration.

In yet another embodiment shown in FIG. 5, a single-sensor, two-eye sequential system 40 includes a single sensor 810 in device 42 to capture both the retina and iris images by employing pulse separation and different wavelengths for the iris and retina. Wavelength multiplexing can be implemented with this embodiment, where a single optic with two surfaces with different coatings permits the capture of different images corresponding to particular wavelengths. For instance, $\lambda_1=810$ nm and $\lambda_3=880$ nm can be used to capture images of the iris, while $\lambda_2=850$ nm and $\lambda_4=910$ nm can be used to capture images of the retina. The two coated surfaces on the single optic permit sequential detection of $\lambda_1$, $\lambda_2$, $\lambda_3$, and $\lambda_4$ and capture of alternating images of the iris and retina. In general, several optical systems can be used to get the images of both eyes on a single detector array. Like the systems described above, the system 40 shown in FIG. 5 employs an LED array 820, a LCD shutter/micro-optics/diffuser 825, a polarizing beamsplitter (PBS) 830, an aspheric objective lens 840, and a single fixation source 310. However, a compensating lens 865, an extra reflective mirror 860, and a dichroic beamsplitter 870 are additionally used in order to form images of the retina and the iris on the same camera sensor 810. The compensation lens allows for proper image magnification for the capture of the iris by camera sensor 810. Moreover, similar to the system 20 of FIG. 3, the system 40 uses a dual retina/iris illumination and retina illumination tracking configuration. The advantage of this system is that it uses a single sensor and fewer parts. However, the disadvantage is that the system runs at half the frame rate for iris and retina image capture being every other frame respectively. In other words, halving the frame rate yields half the number of images of the retina and the iris, so it may be more difficult to obtain adequate images. In addition, this particular configuration must also be flipped like the dual sensor, two-eye flippable configuration shown in FIG. 2.

When the retina illumination tracking system described above is used with symmetric iris/retina camera combinations to allow simultaneous capture of both eyes, such as the two-eye simultaneous system 10 of FIG. 1, one achieves automatic interpupillary adjustment without the need for any moving parts. Interpupillary distance measurement can be determined, providing an additional biometric. With information regarding position along the X- and Y-axes from the pupil tracking algorithm and information regarding position along the Z-axis from the focus measure algorithm, the (X, Y, Z) position of each pupil can be used to calculate pupil separation. As described above, this particular biometric is used to reduce database searching for iris matching, retina matching and iris retina fusion matching. Additional on axis illumination of the iris can also enable bright pupil back reflection ("red eye") that can enhance the iris/retina tracking algorithms.

While all the embodiments above capture and process a combination of iris and retina images, other embodiments of the present invention may capture and process either images of the iris or the retina from both eyes of a subject. As described previously, biometrics based on data from both eyes are more accurate and robust than using biometrics that include data from only the iris or only the retina from a single eye. Illustrating a corresponding exemplary embodiment, FIGS. 6A-D show a device 50 adapted to simultaneously accommodate both eyes of a user, similar to a pair of binoculars, and capture images of both irises. As shown in FIGS. 6A-D, the user employing the device 50 is able to see through the device 50 to view an object external to the device 50 as a target. In particular, with the device positioned at the user's right and left eyes, the user looks into the user windows 902 and through opposing windows 904 to view the external object, or target, on the other side of the device 50. Unlike the embodiments described previously, the device 50 may be employed without a fixation illumination source. The device 50 employs a fixation system where the exit pupil matches or is slightly larger than the entrance pupil of the eye for a given eye relief. Using a two-eyed simultaneous configuration accommodating both eyes, an elliptical, or near elliptical, exit pupil is used to accommodate interpupillary distance. This maintains vertical alignment and allows vergence by the user to maintain horizontal alignment. The target may be an image which appears to be at a distance. Advantageously, this causes the brain to allow the eye to relax to its unaccommodated state.

Figure 6A:
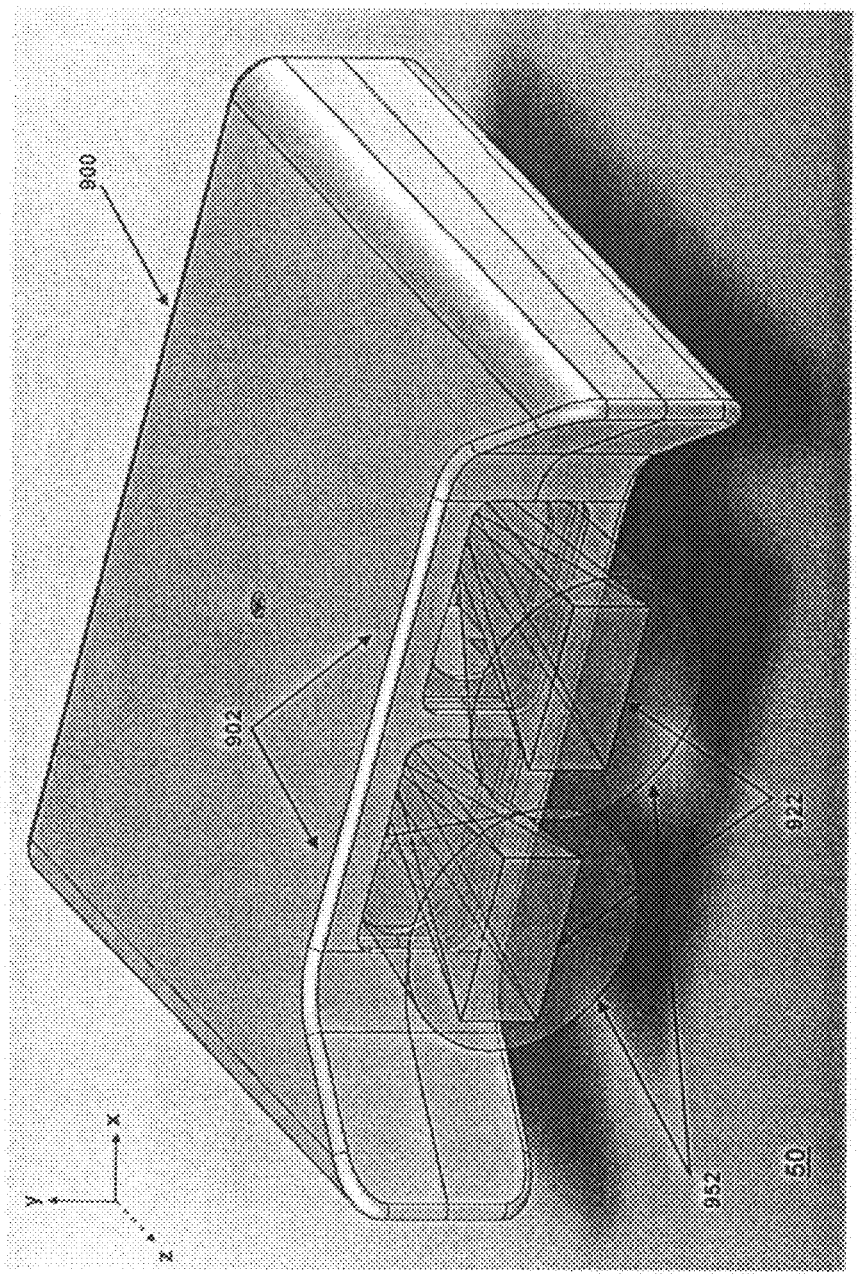
FIG. 6A illustrates an external view of an embodiment of the present invention that captures iris images from both eyes.

In particular, FIG. 6A shows the biometric device 50 with housing 900. In general, users begin by looking through the user windows 902 and bringing the device 50 closer to their eyes until they are able to use their vergence to visually fuse the exit pupils of the device 50. This approach aligns most users to a given image plane with or without eyeglasses. As shown in FIG. 6B, the device 50 also has opposing windows 904 facing the opposing user windows 902. The opposing windows 904 not only permit an image of the target on the other side of the device 50 to be seen by the user, but the opposing windows also allow one to see the eyes of the user positioned at user windows 902. As a result, in addition to operation of the device 50 directly by the user, the device 50 also permits operation by another person who holds the device 50 at the user's face and aligns it to the user's eyes from the other side. Thus, the device 50 allows an operator to assist a user during alignment and operation of the device 50.

With its binocular-like shape, the device 50 helps to ensure proper alignment about at least two axes of rotation in order to achieve a better biometric. With reference to the X-, Y-, and Z-axes shown in FIG. 6A, when users bring the device 50 to their face, they have to position the device 50 so that they can see through both user windows 902, thus ensuring proper alignment about the Z-axis. Moreover, in order to look into the device 50 more easily, users naturally position the device 50 so that the user windows 902 are approximately the same distance from each respective eye, which ensures proper alignment about the Y-axis. As described above, the exit pupils can then be elliptical, or slit-like, to minimize-any misalignment about the X-axis.

Additionally, to obtain more precise alignment of the user's eyes, a linear horizontal diffraction grating, or equivalent "microlouver" technology, may be placed on user windows 902 in order to limit the field of view of the user or operator and ensure proper alignment along the vertical Y-axis. A second vertical diffraction grating may also be employed to also ensure proper alignment along the horizontal X-axis. The combination of horizontal and vertical gratings limits the field of view vertically and horizontally. Moreover, a semitransparent target may be placed behind the gratings for additional alignment indicators.

FIG. 6D illustrates an arrangement of components that may be employed by device 50 to capture images of the irises of both eyes positioned at user windows 902. Two camera sensors 910 with filters 912 are positioned on opposite (right and left) sides in the interior of the device 50 to capture respective images of the right and left eyes. The LEDs 920 provide near infrared illumination to the iris of each eye. The illumination is reflected from the irises back to the respective beamsplitters 930. The beamsplitters 930 may be "hot" mirrors which redirect the near infrared light reflected from the irises to the respective camera sensors 910, but which allow visible light to pass through to the operator windows 904 so that an operator can see the user's eyes. White light illumination from the white light illumination sources 950 may be employed to close down the pupil of the user to provide better biometric data and to help illuminate the eye for alignment by an operator. As shown in FIGS. 6A and 6D, the area 922 of near infrared light cast by the LEDs 920 is smaller than area 952 of white light cast by sources 950. With a smaller area 922, the amount of near infrared light reflected from the area outside the iris, such as the user's cheeks, is minimized.

In order to facilitate the use of the device 50 by an individual who requires corrective eyeglasses, the device 50 may accommodate the individual's eyeglasses 7, as illustrated in FIG. 6C. For instance, the individual's eyeglasses 7 may be combined with the device 50 beyond the beamsplitters 930 but in a position where the eyeglasses can sufficiently correct the person's vision in order to use the device 50 and view the external object. Accordingly, illumination and image capture are not affected by the eyeglasses.

It is understood that a device similar to the device 50 illustrated in FIGS. 6A-D may be used to capture images of the retina from both eyes. Of course, another similar device may be employed to capture images of both the iris and the retina of both eyes, in a manner similar to embodiments described previously.

As described above with reference to FIG. 1, the controller 15 may be a programmable processing device, such as an external conventional computer networked with the device 12 or an on-board field programmable gate array (FPGA) or digital signal processor (DSP), that executes software, or stored instructions. Controllers 25, 35, and 45 shown in FIGS. 3, 4, and 5, respectively, may be similarly configured. In general, physical processors and/or machines employed by embodiments of the present invention for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments of the present invention, as is appreciated by those skilled in the computer and software arts. The physical processors and/or machines may be externally networked with the image capture device, or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present invention may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the exemplary embodiments of the present inventions can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present inventions can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present invention has been described in connection with a number of exemplary embodiments, and implementations, the present inventions are not so limited, but rather cover various modifications, and equivalent arrangements, which fall within the purview of prospective claims. For example, the positions of the iris camera and the fixation illumination source in embodiments above may be switched by the use of a "hot" mirror which reflects the iris image. Similarly, the positions of the retina camera and the retina illumination may be switched by illuminating the retina with P polarized light and imaging the S polarized light.

As a further example, while embodiments may capture retina images from both eyes, only the best retinal image from both eyes may be retained to ensure useable retinal biometric data. As a result, for a two-eye simultaneous configuration, the embodiment produces data regarding the pupillary distance as well as biometric data from both irises and one of the two retina.

Moreover, although the exemplary embodiments discussed herein are combination retina and iris imaging systems used for human identification, the multimodal ocular biometric system of the present invention is not limited to human identification and can be used for animal identification.

What is claimed is:

1. A system for multimodal biometric identification, the system comprising:
    at least one iris imaging system, each iris imaging system including:
        an iris illumination source adapted to emit iris photons to an iris of a right eye or a left eye; and
        an iris image sensor adapted to capture an image of the iris when the iris reflects the iris photons, the image of the iris having iris biometric data;
    at least one retina imaging system, each retina imaging system including:
        a retina illumination source adapted to emit retina photons to a retina of the right eye or the left eye; and
        a retina image sensor adapted to capture an image of the retina when the retina reflects the retina photons, the image of the retina having retinal biometric data; and
    a controller adapted to control the at least one iris imaging system and the at least one retina imaging system,
    wherein the iris image sensor of the at least one iris imaging system captures the image of the iris according to operation of the corresponding iris illumination source, and
    the retina image sensor of the at least one iris imaging system captures the image of the retina according to operation of the corresponding retina illumination source;
    the iris illumination source is operated by the controller with minimal introduction of noise to the operation of the retina illumination source; and
    the retina illumination source is operated by the controller with minimal introduction of noise to the operation of the iris illumination source.

2. The system according to claim 1, wherein the controller pulses the iris illumination source of the at least one iris imaging system and the retina illumination source of the at least one retina imaging system.

3. The system according to claim 2, wherein the controller pulses, with a synchronized offset, the iris illumination source and the retina illumination source.

4. The system according to claim 3, wherein the iris photons emitted by the iris illumination source and the retina photons emitted by the retina illumination source have a same wavelength.

5. The system according to claim 2, wherein the iris illumination source emits the iris photons with a first wavelength and the retina illumination source emits the retina photons with a second wavelength.

6. The system according to claim 5, wherein the controller pulses the iris illumination source and the retina illumination source with a same frequency.

7. The system according to claim 5, wherein the controller pulses the iris illumination source at a first frequency and the retina illumination source at a second frequency.

8. The system according to claim 2, wherein the controller pulses the iris illumination source and the retina illumination source during a same period, and the iris illumination source emits the iris photons with a first wavelength and the retina illumination source emits the retina photons with a second wavelength.

9. The system according to claim 2, wherein the controller alternately pulses the iris illumination source and the retina illumination source, while having the iris illumination source step through a first series of wavelengths for emission of the iris photons with each pulse, and having the retina illumination source step through a second series of wavelengths for emission of the retina photons with each pulse.

10. The system according to claim 1, wherein the controller controls the iris illumination source of the at least one iris imaging system to emit the iris photons in a continuous wave and the retina illumination source of the at least one retina imaging system to emit the retina photons in a continuous wave, and the iris illumination source emits the iris photons with a first wavelength and the retina illumination source emits the retina photons with a second wavelength.

11. The system according to claim 1, wherein the iris photons emitted by the iris illumination source of the at least one iris imaging system and the retina photons emitted by the retina illumination source of the at least one retina imaging system have a near-infrared wavelength.

12. The system according to claim 1, wherein the iris illumination source of the at least one iris imaging system emits the iris photons with more than one wavelength, and the retina illumination source of the at least one retina imaging system emits the retina photons with more than one wavelength.

13. The system according to claim 1, wherein at least one of the iris illumination source of the at least one iris imaging system and the retina illumination source of the at least one retina imaging system comprises a light emitting diode (LED) array.

14. The system according to claim 1, wherein at least one of the iris illumination source of the at least one iris imaging system and the retina illumination source of the at least one retina imaging system comprises a laser diode.

15. The system according to claim 1, wherein at least one of the iris image sensor of the at least one iris imaging system and the retina image sensor of the at least one retina imaging system comprises a complementary metal-oxide semiconductor (CMOS) detector.

16. The system according to claim 1, wherein at least one of the iris image sensor of the at least one iris imaging system and the retina image sensor of the at least one retina imaging system comprises a charge-coupled device (CCD) detector.

17. The system according to claim 1, wherein at least one of the iris photons emitted by the iris illumination source of the at least one iris imaging system and the retina photons emitted by the retina illumination source of the at least one retina imaging system passes through a refractive lens.

18. The system according to claim 1, wherein at least one of the iris photons emitted by the iris illumination source of the at least one iris imaging system and the retina photons emitted by the retina illumination source of the at least one retina imaging system reflect off a reflective mirror.

19. The system according to claim 1, further comprising a processor adapted to measure a focus of the image of the iris captured by the at least one iris imaging system.

20. The system according to claim 1, further comprising a processor adapted to determine a position for a pupil of the eye from the image of the iris captured by the at least one iris imaging system.

21. The system according to claim 20, wherein the retina illumination source of one of the at least one retina imaging system emits the retina photons to a corresponding retina of the eye based on the determined position for the pupil of the eye.

22. The system according to claim 20, wherein the retina illumination source of one of the at least one retina imaging system comprises an array of LED's, each element of the array corresponding to a set of pupil positions, and the retina illumination source of the retina imaging system emits the retina photons to a corresponding retina of the eye, the retina photons being emitted from an element of the array according to the determined position for the pupil of the eye.

23. The system according to claim 1, wherein the controller applies auto gain to correct for iris and retina reflectance differences.

24. The system according to claim 1, wherein the controller pulses at least one of the iris illumination source of the at least one iris imaging system and the retina illumination source of the at least one retina imaging system through a cycle of more than one illumination power settings to correct for iris and retina reflectance differences.

25. The system according to claim 1, wherein the controller pulses at least one of the iris illumination source of the at least one iris imaging system and the retina illumination source of the at least one retina imaging system through a cycle of more than one pulse durations to correct for iris and retina reflectance differences.

26. The system according to claim 1, further comprising an auto focus system for at least one of the at least one iris imaging system and the at least one retina imaging system including an imaging lens and a motorized lens adapted to move the focus of the imaging lens.

27. The system according to claim 26, wherein the motorized lens moves the focus of the imaging lens according to a corresponding focus measurement of at least one of the iris and the retina.

28. The system according to claim 1, further comprising an auto focus system for at least one of the at least one iris imaging system and the at least one retina image sensor of the at least one retina imaging system comprising a processor adapted to apply digital filters to the captured image based on wavefront coding technology.

29. The system according to claim 1, further comprising an auto focus system for at least one of the at least one iris imaging system and the at least one retina imaging system comprising an electro-active optical element.

30. The system according to claim 29, wherein the electro-active optical element comprises a liquid crystal in between two pieces of glass with an electrode configuration.

31. The system according to claim 1, further comprising a fixation system to position at least one of the right eye and the left eye of a user.

32. The system according to claim 31, wherein the fixation system further comprises at least one exit pupil that substantially matches an entrance pupil of the right eye or the left eye for a given eye relief.

33. The system according to claim 31, wherein the fixation system further comprises at least one elliptical exit pupil that accommodates interpupillary distance, to maintain vertical alignment of the user and to allow vergence by the user to maintain horizontal alignment.

34. The system according to claim 33, further comprising a viewing target for the user.

35. The system according to claim 31, wherein the fixation system provides visual and aural signals to the user based on a determined position of a pupil and on a focus measurement of at least one of the iris and the retina of the right eye or the left eye.

36. The system according to claim 31, wherein the fixation system comprises:
a processor adapted to determine a position of a pupil of a user and to measure a focus of at least one of the iris and the retina; and
a display with a first visual indicator indicating a nominal position for the user, and a second visual indicator indicating the position of the user determined by the processor,
wherein the second visual indicator moves on the display as the user moves, and overlaps with the first visual indicator when the user moves into the nominal position.

37. The system according to claim 36, wherein at least one of the first visual indicator and the second visual indicator comprises cross hairs.

38. The system according to claim 37, wherein the second visual indicator further comprises a circle, the circle having a diameter that increases or decreases according to movement by the user relative to the nominal position.

39. The system according to claim 36, further comprising aural signals indicating the position of the user relative to the nominal position.

40. The system according to claim 31, wherein the fixation system accommodates eyeglasses.

41. The system according to claim 1, further comprising a personal identification number (PIN) entry system that accepts a user's PIN by tracking the position of the user's pupil as the user focuses on symbols on a display.

42. The system according to claim 1, wherein a single illumination source includes the iris illumination source of the at least one iris imaging system and the retina illumination source of the at least one retina imaging system, and a single image sensor includes the iris image sensor of the at least one iris imaging system and the retina image sensor of the at least one retina imaging system.

43. The system according to claim 42, further comprising a compensating lens, an reflective mirror, and a beamsplitter to form the iris image and the retina image on the single camera sensor.

44. The system according to claim 1, wherein the at least one iris imaging system includes two iris imaging systems, the at least one retina imaging system includes two retina imaging systems, and the two iris imaging systems and the two retina imaging systems operate at least substantially simultaneously to capture a set of iris images and retina images from both the right eye and the left eye, the set of iris images and retina images providing biometric data.

45. The system according to claim 44, further comprising a processor adapted to determine at least one of interpupillary distance and limbus diameter from the biometric data.

46. The system according to claim 45, further comprising:
  means for creating subsets of data, from reference data in a biometric database, according to ranges of at least one of interpupillary distance and limbus diameter;
  means for determining at least one of an interpupillary distance measurement and a limbus diameter measurement for the user; and
  means for searching one of the subsets of data containing at least one of the interpupillary distance measurement and the limbus diameter measurement for a biometric match within the reference data.

47. The system according to claim 1, wherein the at least one iris imaging system includes one iris imaging system corresponding to both the right eye and the left eye, the at least one retina imaging system includes two retina imaging systems corresponding to the right eye and the left eye, respectively, and the controller controls the one iris imaging systems to operate with one of the two retina imaging systems to capture a set of iris images and retina images from one of the right eye and the left eye, the set of iris images and retina images providing biometric data.

* * * * *